US008680146B2

(12) United States Patent
Jordine et al.

(10) Patent No.: US 8,680,146 B2
(45) Date of Patent: Mar. 25, 2014

(54) ORGANIC COMPOUNDS

(75) Inventors: Guido Jordine, Freiburg (DE); Michael Mutz, Freiburg (DE)

(73) Assignee: Novartis AG, Basel (CH)

( * ) Notice: Subject to any disclaimer, the term of this patent is extended or adjusted under 35 U.S.C. 154(b) by 29 days.

(21) Appl. No.: 13/128,832

(22) PCT Filed: Nov. 10, 2009

(86) PCT No.: PCT/EP2009/064889
§ 371 (c)(1),
(2), (4) Date: May 11, 2011

(87) PCT Pub. No.: WO2010/055027
PCT Pub. Date: May 20, 2010

(65) Prior Publication Data
US 2011/0218248 A1     Sep. 8, 2011

(30) Foreign Application Priority Data

Nov. 11, 2008 (EP) .................................. 08168862

(51) Int. Cl.
| | |
|---|---|
| *A61K 31/192* | (2006.01) |
| *A61K 31/19* | (2006.01) |
| *A61K 31/194* | (2006.01) |
| *C07C 63/08* | (2006.01) |
| *C07C 59/255* | (2006.01) |
| *C07C 55/10* | (2006.01) |
| *C07C 55/08* | (2006.01) |

(52) U.S. Cl.
USPC ........... 514/568; 514/557; 514/574; 562/493; 562/585; 562/589; 562/590

(58) Field of Classification Search
USPC .......... 514/568, 557, 574; 562/493, 585, 589, 562/590
See application file for complete search history.

(56) References Cited

U.S. PATENT DOCUMENTS

6,605,744 B2 *  8/2003  Abel et al. ..................... 564/357
7,985,586 B2 *  7/2011  Bieberich ..................... 435/366

FOREIGN PATENT DOCUMENTS

| EC | SP 95-1461 | 4/1998 |
| EC | SP 97-2265 | 11/1998 |
| EP | A-0627406 | 12/1994 |
| WO | 0027796 A1 | 5/2000 |
| WO | WO 03/097028 | 11/2003 |
| WO | WO2004089341 | 10/2004 |
| WO | WO2007021666 | 2/2007 |
| WO | WO 2007/143081 | 12/2007 |

OTHER PUBLICATIONS

Correa, C., "Guidelines for the examination of pharmaceutical patents: developing a public health perspective", University of Buenos Aires, p. 9. Found in: http://ictsd.org/downloads/2008/06/correa_patentability20guidelines.pdf.
Kiuchi M et al. "Synthesis and Immunosuppressive Activity of 2-Substituted 2-Aminopropane-1,3-diols and 2-Aminoethanols" Journal of Medicinal Chemistry, American Chemical Soc., pp. 2946-2961. XP002271142, 2000.
Bastin et al., "Salt Selection and Optimization Procedures for Pharmaceutical New Chemical Entities", Organic process Research and Development, vol. 4, No. 5, 2000, p. 427-435.
Haynes et al., "Occurrence of Pharmaceutically Acceptable anions and Cations in the Cambridge Database", Journal of Pharmaceutical Sciences, vol. 94, No. 10, 2005, p. 2111-2120.
Polymorphism in pharmaceutical solids edited by H. G. Brittain, Marcel Dekker, (1999), D. J. W. Grant (chapter 1) p. 1-10; K. R. Morris (chapter 4) p. 125-181 and J. K. Guillory (chapter 5) p. 183-226.
S. M. Byrn et al., Pharmaceutical Solids: a strategic Approach to Regulatory Considerations, Pharmaceutical Research, vol. 12, No. 7, 1995, p. 945-954.

* cited by examiner

*Primary Examiner* — Jennifer M Kim
(74) *Attorney, Agent, or Firm* — Andrew Holmes (57) ABSTRACT

The present invention relates to salts, polymorphs and hydrates of 2-Amino-2-[2-(4-$C_{2-20}$-alkyl-phenyl)ethyl]propane-1,3-diol, and to the use thereof, in particular in the treatment or prevention of various autoimmune conditions.

7 Claims, 7 Drawing Sheets

ORGANIC COMPOUNDS

The present invention relates to salts, e.g. crystalline salts, of the compound FTY720, and to the use thereof.

2-Amino-2-[2-(4-$C_{2-20}$-alkyl-phenyl)ethyl]propane-1,3-diol compounds are disclosed in EP-A-0627406, the relevant disclosure of which is incorporated herein by reference. On the basis of observed activity, the compounds have been found to be useful as immunosuppressants. Accordingly, the compounds may be useful in the treatment or prevention of various autoimmune conditions, including multiple sclerosis. A particular compound in this class is FTY720 (2-amino-2-[2-(4-octylphenyl)ethyl]propane-1,3-diol fingolimod), which may be obtained in the form of the free base or a hydrochloride salt. The structure of FTY720 is shown below:

According to the present invention, there is provided a crystalline salt of FTY720, wherein the salt is selected from tartrate, lactate, benzoate, succinate, malonate, acetate and propionate salts, and the salt is optionally crystalline.

In an embodiment, the salt is selected from tartrate, lactate, benzoate, succinate and malonate salts.

In another embodiment, the salt is selected from tartrate, lactate, succinate and malonate salts.

in an embodiment, the salt is a tartrate salt.

BRIEF DESCRIPTION OF THE DRAWINGS

In a specific embodiment, the salt is a tartrate salt characterised by an X-ray powder diffraction pattern having peaks at least two, preferably at least four, and more preferably all, of the following 2-theta values: about 3.1, 19.3, 21.7, 9.6, 17.2, 6.4, 22.6 and 20.8 degrees 2-theta. The peaks at said 2-theta values may have the following relative intensities: 3.1 (strong), 19.3 (weak), 21.7 (weak), 9.6 (weak), 17.2 (weak), 6.4 (weak), 22.6 (weak) and 20.8 (weak). In a particular embodiment, the salt is a tartrate salt characterised by an X-ray powder diffraction pattern corresponding substantially to that shown in FIG. 1.

In an embodiment, the salt is a lactate salt.

In a specific embodiment, the salt is a lactate salt characterised by an X-ray powder diffraction pattern having peaks at at least two, preferably at least four, and more preferably all, of the following 2-theta values: 4.3, 8.7, 20.8, 13.1, 10.3, 18.8, 8.1, 21.6, 21.9 and 19.6 degrees 2-theta. The peaks at said 2-theta values may have the following relative intensities: 4.3 (strong), 8.7 (medium), 20.8 (medium), 13.1 (medium), 10.3 (weak), 18.8 (weak), 8.1 (weak), 21.6 (weak), 21.9 (weak) and 19.6 (weak). In a particular embodiment, the salt is a lactate salt characterised by an X-ray powder diffraction pattern corresponding substantially to that shown in FIG. 2.

In an embodiment, the salt is a benzoate salt.

In a specific embodiment, the salt is a benzoate salt characterised by an X-ray powder diffraction pattern with peaks at at least two, preferably at least four, and more preferably all, of the following 2-theta values: 3.7, 7.5, 18.7, 19.8, 15.2, 19.4, 19.9, 6.0 and 21.9 degrees 2-theta. The peaks at said 2-theta values may have the following relative intensities: 3.7 (strong), 7.5 (medium), 18.7 (weak), 19.8 (weak), 15.2 (weak), 19.4 (weak), 19.9 (weak), 6.0 (weak) and 21.9 (weak). In a particular embodiment, the salt is a benzoate salt characterised by an X-ray powder diffraction pattern corresponding substantially to that shown in FIG. 3.

In an embodiment, the salt is a succinate salt.

In a specific embodiment, the salt is a succinate salt characterised by an X-ray powder diffraction pattern having peaks at at least two preferably at least four, and more preferably all, of the following 2-theta values: 3.2, 19.8, 20.7, 23.3, 26.2, 9.8, 19.4, 24.5, 33.4, 26.6 and 22.6 degrees 2-theta. The peaks at said 2-theta values may have the following relative intensities: 3.2 (strong), 19.8 (medium), 20.7 (weak), 23.3 (weak), 26.2 (weak), 9.8 (weak), 19.4 (weak), 24.5 (weak), 33.4 (weak), 26.6 (weak) and 22.6 (weak). In a particular embodiment, the salt is a succinate salt characterised by an X-ray powder diffraction pattern corresponding substantially to that shown in FIG. 4.

In an embodiment, the salt is a malonate salt.

In a specific embodiment, the salt is a malonate salt characterised by an X-ray powder diffraction pattern having peaks at at least two, preferably at least four, and more preferably all, of the following 2-theta values: 2.5, 5.2, 8.0, 16.2, 17.0, 20.4 degrees 2-theta. The peaks at said 2-theta values may have the following relative intensities: 2.5 (strong), 5.2 (weak), 8.0 (weak), 16.2 (weak), 17.0 (weak), 20.4 (weak). In a particular embodiment, there is provided a malonate salt characterised by an X-ray powder diffraction pattern corresponding substantially to that shown in FIG. 5.

In an embodiment, the salt is an acetate salt.

In a specific embodiment, the salt is an acetate salt characterised by an X-ray powder diffraction pattern having peaks at at least two, preferably at least four, and more preferably all, of the following 2-theta values: 4.8, 8.4, 10.1, 11.5, 15.2, 17.7, 19.3, 20.1, 21.5, 21.9, 24.0, 25.4, degrees 2-theta. The peaks at said 2-theta values may have the following relative intensities: 4.8 (strong), 8.4 (weak), 10.1 (medium), 11.5 (weak), 15.2 (medium), 17.7 (weak), 19.3 (weak), 20.1 (weak), 21.5 (weak), 21.9 (weak), 24.0 (weak), 25.4 (medium), 30.8 (weak). In a particular embodiment, there is provided an acetate salt characterised by an X-ray powder diffraction pattern corresponding substantially to that shown in FIG. 6.

In an embodiment, the salt is a propionate salt.

In a specific embodiment, the salt is a propionate salt characterised by an X-ray powder diffraction pattern having peaks at at least two, preferably at least four, and more preferably all, of the following 2-theta values: 4.8, 8.4, 9.8, 14.7, 16.8, 17.6, 19.7, 20.2, 22.6, 24.8, 29.8 degrees 2-theta. The peaks at said 2-theta values may have the following relative intensities: 4.8 (strong), 8.4 (weak), 9.8 (medium), 14.7 (weak), 16.8 (weak), 17.6 (weak), 19.7 (weak), 20.2 (weak), 22.6 (weak), 24.8 (weak), 29.8 (weak). In a particular embodiment, there is provided a propionate salt characterised by an X-ray powder diffraction pattern corresponding substantially to that shown in FIG. 7.

Advantageously, the various salt forms of the invention may have one or more desirable properties compared with the free base form or hydrochloride form of FTY720. For example, the salts may be more stable and of better quality than the free base, in particular during storage and distribution. In addition, the salts may have a high degree of dissociation in water and thus substantially improved water solubility. The present salts may also be advantageous in that they show no measurable water absorption or loss.

Crystalline forms may be characterized by the major peaks of an X-ray powder diffraction spectrum, as illustrated in the Examples herein. Crystalline forms may also differ with respect to their thermodynamic stability, in their physical parameters, such as the absorption pattern in an infrared spectroscopy (IR) or phase transition signals in differential scanning calorimetry (DSC). Salts of the present invention are preferably in substantially pure crystalline form. The term "substantially pure" as used herein includes reference to crystalline forms of greater than 90%, more preferably 95%, more preferably 96%, more preferably 97%, more preferably 98%, more preferably 99% polymorphic purity as determined, for example, by X-ray powder diffraction, Raman spectroscopy or IR spectroscopy.

Salts of the invention may be in the form of solvates, including hydrates, and may exhibit polymorphism.

Salts of the present invention may be synthesized from the free base by conventional chemical methods. Generally, such salts can be prepared by reacting the free base form of FTY720 with the appropriate acid in water or in an organic solvent, or in a mixture of the two. In many cases, non-aqueous media, for example ethyl acetate, ethanol or isopropanol may be used. FTY720 and the acid are combined in the desired stoichiometric ratio, for example 1:1 or 1:2. The salt may then be allowed or induced to crystallise or form an amorphous solid, optionally prior to crystallisation. The solid salt may then be dried, e.g. by heating under reduced pressure. By way of illustration, and without limitation, the various salt forms of the invention may be obtained according to the procedures given in the Examples herein.

Also provided are pharmaceutical formulations comprising a crystalline salt of the invention. A pharmaceutical formulation of the invention preferably contains 0.01 to 20% by weight of the salt, more preferably 0.1 to 10%, e.g. 0.5 to 5% by weight, based on the total weight of the formulation.

The pharmaceutical formulation may be a solid pharmaceutical composition in a form suitable for oral administration, e.g. a tablet or capsule. The composition may be manufactured in a conventional manner, e.g. by mixing a salt of the invention with a pharmaceutically acceptable carrier or diluent.

In a particular embodiment, the formulation is a solid pharmaceutical composition comprising a salt of the invention and a sugar alcohol. Compositions of this type are disclosed in WO 2004/089341, the contents of which are incorporated herein by reference. The solid compositions disclosed in this publication are particularly well suited to the oral administration of the salts of the present invention. The compositions provide a convenient means of systemic administration of the compounds, do not suffer from the disadvantages of liquid formulations for injection or oral use, and have good physicochemical and storage properties. In particular, the compositions of the present invention may show a high level of uniformity in the distribution of the compound throughout the composition, as well as high stability. The compositions may therefore be manufactured on high speed automated equipment, and thus do not require hand encapsulation.

The sugar alcohol may act as a diluent, carrier, filler or bulking agent, and may suitably be mannitol, maltitol, inositol, xylitol or lactitol, preferably a substantially non-hygroscopic sugar alcohol, e.g. mannitol (D-mannitol). A single sugar alcohol may be used, or a mixture of two or more sugar alcohols, e.g a mixture of mannitol and xylitol, e.g. in a ratio of 1:1 to 4.1.

In a particularly preferred embodiment, the sugar alcohol is prepared from a spray-dried composition, e.g. mannitol composition, having a high specific surface area. The use of this type of mannitol composition may assist in promoting uniform distribution of the compound throughout the mannitol in the composition. A higher surface area may be achieved by providing a sugar alcohol, e.g. mannitol, preparation consisting of particles having a smaller mean size and/or a rougher surface on each particle. The use of a spray-dried sugar alcohol, e.g. mannitol, e.g. with a mean particle size of 300 µm or less, has also been found to improve compressibility and hardness of tablets formed from the composition.

Preferably the single point surface area of the sugar alcohol preparation, e.g. mannitol, is 1 to 7 $m^2/g$, e g, 2 to 6 $m^2/g$ or 3 to 5 $m^2/g$. The mannitol preparation may suitably have a mean particle size of 100 to 300 µm, e.g. 150 to 250 µm and a bulk density of 0.4 to 0.6 g/mL, e.g. 0.45 to 0.55 g/mL. A suitable high surface area mannitol is Parteck M200, available commercially from E. Merck.

The composition preferably contains 75 to 99.99% by weight of the sugar alcohol, more preferably 85 to 99.9% e.g. 90 to 99.5% by weight, based on the total weight of the composition.

The composition preferably further comprises a lubricant. Suitable lubricants include stearic acid, magnesium stearate, calcium stearate, zinc stearate, glyceryl palmitostearate, sodium stearyl fumarate, canola oil, hydrogenated vegetable oil such as hydrogenated castor oil (e.g Cutina® or Lubriwax® 101), mineral oil, sodium lauryl sulfate, magnesium oxide, colloidal silicon dioxide, silicone fluid, polyethylene glycol, polyvinyl alcohol, sodium benzoate, talc, poloxamer, or a mixture of any of the above. Preferably the lubricant comprises magnesium stearate, hydrogenated castor oil or mineral oil. Colloidal silicon dioxide and polyethylene glycol are less preferred as the lubricant.

The composition preferably contains 0.01 to 5% by weight of a lubricant, more preferably 1 to 3% by weight, e.g. about 2% by weight, based on the total weight of the composition.

The composition may comprise one or more further excipients such as carriers, binders or diluents. In particular, the composition may comprise microcrystalline cellulose (e.g. Avicel®), methylcellulose, hydroxypropylcellulose, hydroxypropylmethylcellulose, starch (e.g corn starch) or dicalcium phosphate, preferably in an amount of from 0.1 to 90% by weight, e.g. 1 to 30% by weight, based on the total weight of the composition. Where a binder, e.g microcrystalline cellulose, methylcellulose, hydroxypropyl cellulose, hydroxypropylmethyl cellulose is used, it is preferably included in an amount of 1 to 8%, e.g. 3 to 6% by weight, based on the total weight of the composition. The use of a binder increases the granule strength of the formulation, which is particularly important for fine granulations. Micro-crystalline cellulose and methylcellulose are particularly preferred where a high tablet hardness and/or longer disintegration time is required. Hydroxypropyl cellulose is preferred where faster disintegration is required. Where appropriate, xylitol may also be added as an additional binder, for example in addition to microcrystalline cellulose, e.g. in an amount up to 20% by weight of the sugar alcohol, e.g. xylitol.

In one embodiment, the composition further comprises a stabiliser, preferably glycine HCl or sodium bicarbonate. The stabiliser may be present in an amount of e.g. 0.1 to 30%, preferably 1 to 20% by weight.

The composition may be in the form of a powder, granule or pellets or a unit dosage form, for example as a tablet or capsule. The compositions of the present invention are well-adapted for encapsulation into an orally administrable capsule shell, particularly a hard gelatin shell.

Alternatively the compositions may be compacted into tablets. The tablets may optionally be coated, for instance with talc or a polysaccharide (e.g. cellulose) or hydroxypropylmethyl-cellulose coating.

Where a pharmaceutical capsule is in unit dosage form, each unit dosage may, for example, contain from about 0.5 to about 10 mg of a salt of the invention.

The compositions of the invention may show good stability characteristics as indicated by standard stability trials, for example having a shelf life stability of up to one, two or three years, and even longer. Stability characteristics may be determined, e.g. by measuring decomposition products by HPLC analysis after storage for particular times, at particular temperatures, e.g. 20, 40 or 60° C.

The pharmaceutical compositions of the present invention may be produced by standard processes, for instance by conventional mixing, granulating, sugar-coating, dissolving or lyophilizing processes. Procedures which may be used are known in the art, e.g. those described in L. Lachman at al. The Theory and Practice of Industrial Pharmacy, 3rd Ed, 1988. H Sucker et al, Pharmazeutische Technologie, Thieme, 1991, Hagers Handbuch der pharmazeutischen Praxis, 4th Ed. (Springer Veriag, 1971) and Remington's Pharmaceutical Sciences, 13th Ed., (Mack Publ., Co., 1970) or later editions.

In an embodiment, the pharmaceutical composition is produced by a process comprising:
(a) mixing a salt of the invention with a sugar alcohol;
(b) milling and/or granulating the mixture obtained in (a); and
(c) mixing the milled and/or granulated mixture obtained in (b) with a lubricant.

By using this process, a preparation having a good level of content and blend uniformity (i.e. a substantially uniform distribution of the salt throughout the composition), dissolution time and stability is obtained.

The salt may optionally be micronized, and/or pre-screened, e.g. with a 400 to 500 μm mesh screen, before step (a) in order to remove lumps. The mixing step (a) may suitably comprise blending the salt and the sugar alcohol, e.g. mannitol in any suitable blender or mixer for e.g. 100 to 400 revolutions.

The process may be carried out by dry mixing the components. In this embodiment the milling step (b) may suitably comprise passing the mixture obtained in (a) through a screen, which preferably has a mesh size of 400 to 500 μm. Process step (a) may comprise the step of mixing the total amount of the salt at first with a low amount of sugar alcohol, e.g. from 5 to 25% by weight of the total weight of sugar alcohol, in order to form a pre-mix. Subsequently the remaining amount of sugar alcohol is added to the pre-mix. Step (a) may also comprise the step of adding a binder solution, e.g. methylcellulose and/or xylitol, e.g. an aqueous solution, to the mixture. Alternatively the binder is added to the mix dry and water is added in the granulation step.

The milled mixture obtained in (b) may optionally be blended once more before mixing with the lubricant. The lubricant, e.g. magnesium stearate, is preferably pre-screened, e.g. with a 800 to 900 μm screen, before mixing.

Alternatively, a wet granulation process is employed. In this embodiment, the salt is preferably first dry-mixed with the desired sugar alcohol, e.g. mannitol, and the obtained sugar alcohol/salt mixture is then dry-mixed with a binder such as hydroxypropyl cellulose or hydroxypropylmethyl cellulose. Water is then added and the mixture granulated, e.g. using an automated granulator. The granulation is then dried and milled.

If desirable, an additional amount of binder may be added in step (c) to the mixture obtained in (b).

The process may comprise a further step of tabletting or encapsulating the mixture obtained in (c), e.g. into a hard gelatin capsule using an automated encapsulation device. The capsules may be coloured or marked so as to impart an individual appearance and to make them instantly recognizable. The use of dyes can serve to enhance the appearance as well as to identify the capsules. Dyes suitable for use in pharmacy typically include carotinoids, iron oxides, and chlorophyll. Preferably, the capsules of the invention are marked using a code.

Salts of the invention may be useful in:
a) treatment and prevention of organ or tissue transplant rejection, for example for the treatment of the recipients of heart, lung, combined heart-lung, liver, kidney, pancreatic, skin or corneal transplants, and the prevention of graft-versus-host disease, such as sometimes occurs following bone marrow transplantation; particularly in the treatment of acute or chronic allo- and xenograft rejection or in the transplantation of insulin producing cells, e.g. pancreatic islet cells; and
b) treatment and prevention of autoimmune disease or of inflammatory conditions, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis. Graves ophthalmopathy, alopecia areata and others, allergic diseases, e.g. allergic asthma, atopic dermatitis, allergic rhinitis/conjunctivitis, allergic contact dermatitis, inflammatory diseases optionally with underlying aberrant reactions, e.g. inflammatory bowel disease. Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises seborrhoeic dermatitis, cutaneous manifestations of immunologically-mediated disorders, inflammatory eye disease, keratoconjunctivitis, myocarditis or hepatitis.

For the above uses the required dosage will of course vary depending on the mode of administration, the particular condition to be treated and the effect desired. In general, satisfactory results are indicated to be obtained at daily dosages of from about 0.1 to about 100 mg/kg body weight. An indicated daily dosage in the larger mammal, e.g. humans, is in the range of from about 0.5 mg to 2000 mg, conveniently administered, for example, in divided doses up to four times a day or in retard form.

The salts may be administered by any appropriate route, e.g. orally, for example in the form of a tablet or capsule, topically or parenterally, for example intravenously. Pharmaceutical compositions comprising a salt of the invention in association with at least one pharmaceutically acceptable carrier or diluent may be manufactured in conventional manner by mixing with a pharmaceutically acceptable carrier or diluent. Unit dosage forms for oral administration contain, for example, from about 0.1 mg to about 500 mg of active substance.

The salts may be administered as the sole active ingredient or together with other drugs in immunomodulating regimens or other anti-inflammatory agents e.g. for the treatment or prevention of allograft acute or chronic rejection or inflammatory or autoimmune disorders. For example, they may be used in combination with calcineurin inhibitors, e.g. cyclosporin A, cyclosporin G, FK-506, ABT-281, ASM 981; an mTOR inhibitor, e.g. rapamycin, 40-O-(2-hydroxy)ethyl-rapamycin, CCI779, ABT578 or AP23573 etc.; corticosteroids; cyclophosphamide; azathioprene; methotrexate; another S1P receptor agonist, e.g. FTY 720 or an analogue thereof; leflunomide or analogs thereof; mizoribine; mycophenolic acid; mycophenolate mofetil; 15-deoxyspergualine or analogs thereof; immunosuppressive monoclonal antibodies, e.g., monoclonal antibodies to leukocyte receptors, e.g., MHC, CD2, CD3, CD4, CD 11a/CD18, CD7, CD25, CD 27, B7, CD40, CD45, CD58, CD 137, ICOS, CD150 (SLAM), OX40, 4-1BB or their ligands, e.g. CD154; or other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y, or other adhesion molecule inhibitors, e.g. mAbs or low molecular weight inhibitors including LFA-1 antagonists, Selectin antagonists and VLA-4 antagonists.

Where a salt is administered in conjunction with another immunomodulating or anti-inflammatory agent, dosages of the co-administered immunomodulating or anti-inflammatory agent will of course vary depending on the type of co-drug employed, on the condition to be treated and so forth.

The present invention thus provides:

1. A method of treating or preventing organ or tissue transplant rejection, comprising administering to a subject a therapeutically effective amount of a crystalline salt of the invention.
2. A method of treating or preventing an autoimmune disease or inflammatory condition, comprising administering to a subject a therapeutically effective amount of a crystalline salt of the invention.
3. A salt of the invention, e.g. a crystalline salt of the invention, for use as a pharmaceutical.
4. A pharmaceutical composition comprising a salt of the invention, e.g. a crystalline salt of the invention, and a pharmaceutically acceptable diluent or carrier.
5. Use of a salt of the invention, e.g. a crystalline salt of the invention for the preparation of a medicament, e.g. in a method as disclosed above.
6. A pharmaceutical combination comprising (a) a salt of the invention, e.g. a crystalline salt of the invention and (b) a second drug substance, said second drug substance being suitable for the prevention or treatment of a condition described above.
7. A method as defined above comprising co-administration, e.g. concomitantly or in sequence, of (a) a crystalline salt of the invention and (b) a second drug substance, said second drug substance being suitable for the prevention or treatment of a condition described above.

The following Examples illustrate the invention. In Examples 1 to 29 references to Compound A FTY720 or FTY720 hydrochloride salt should be taken to include reference to any of the various salts of the present invention.

EXAMPLE 1

Micronized Compound A, e.g. 2-amino-2-[2-(4-octylphenyl)ethyl]propane-1,3-diol hydrochloride salt (FTY720), is screened and 116.7 g of the screened compound is mixed with 9683.3 g of a microcrystalline cellulose agent. The mixture is then milled in a Frewitt MGI device (Key International Inc. USA) using a 30 mesh screen. Magnesium stearate is screened using a 20 mesh screen and 200 g of the screened compound blended with the FTY720 mixture to produce a product composition.

The product composition is then compacted on a tablet press using a 7 mm die to form 120 mg tablets, each containing:

| | |
|---|---|
| Compound A, e.g. FTY720 * | 1.4 mg |
| Microcrystalline cellulose, e.g. Avicel PH 102 | 116.2 mg |
| Magnesium stearate | 2.4 mg |
| Total | 120 mg |

* 1 mg of Compound A in free form is equivalent to 1.12 mg of FTY720.

EXAMPLE 2

In a further example, the process of example 1 is repeated except that the magnesium stearate is replaced by Cutina® (hydrogenated castor oil).

EXAMPLE 3

FTY720 Tartrate

The tartrate salt was then analysed by X-ray powder diffraction (XRPD). In this and the following Examples, X-ray powder diagrams were recorded between 2° and 35° (2 theta) with Cu Kα radiation using a Scintag X1 diffraction system. Temperature variable and humidity variable XRPD was performed using the Scintag XDS 2000 system equipped with a temperature and humidity control unit.

Figure 1:
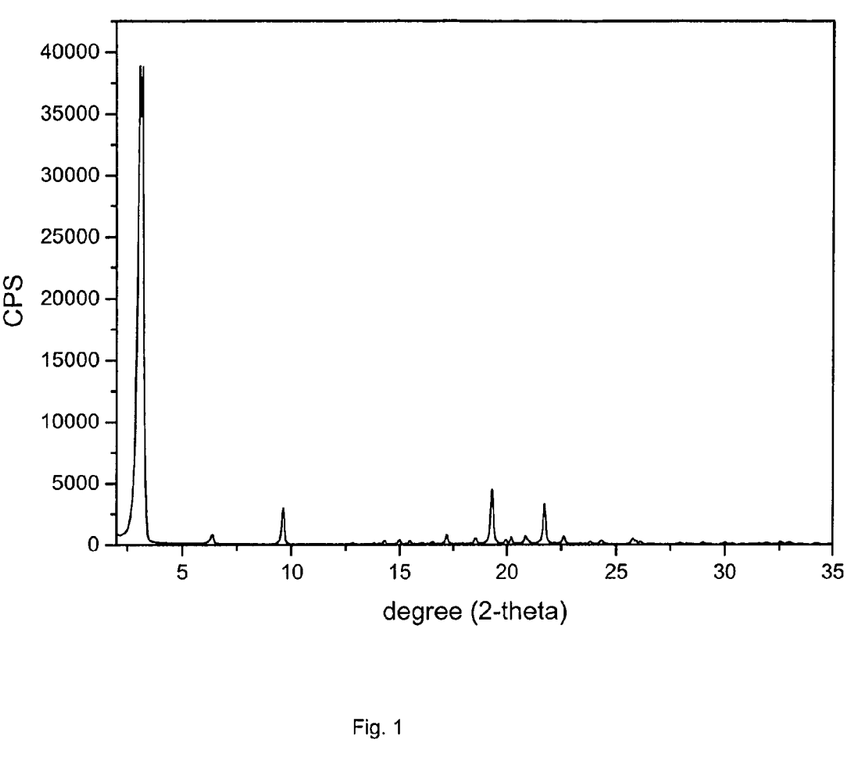

The XRPD diagram of FTY720 tartrate is shown in FIG. 1, with significant peaks given below:

| 2-theta (deg) | d-spacing (Å) | Rel. Intensity |
|---|---|---|
| 3.1 | 28.664 | Strong |
| 19.3 | 4.596 | Weak |
| 21.7 | 4.092 | Weak |
| 9.6 | 9.221 | Weak |
| 17.2 | 5.158 | Weak |
| 6.4 | 13.906 | Weak |
| 22.6 | 3.931 | Weak |
| 20.8 | 4.258 | Weak |

EXAMPLE 4

FTY720 Lactate

Figure 2:
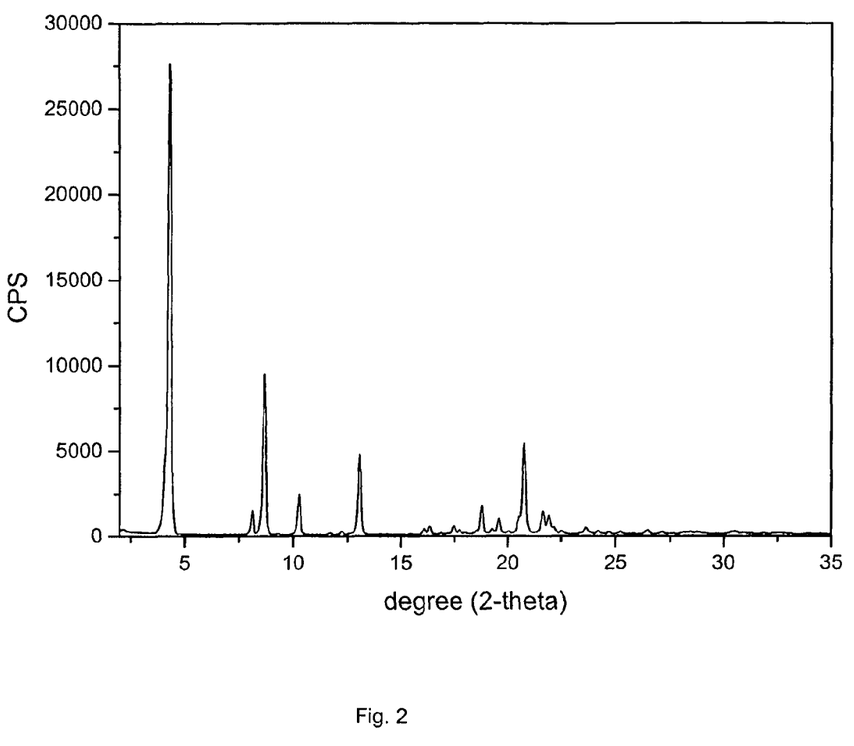

The XRPD diagram of FTY720 lactate is shown in FIG. 2, with significant peaks given below:

| 2-theta (deg) | d-spacing (Å) | Rel. Intensity |
|---|---|---|
| 4.3 | 20.493 | Strong |
| 8.7 | 10.183 | Medium |
| 20.8 | 4.272 | Medium |
| 13.1 | 6.768 | Medium |
| 10.3 | 8.587 | Weak |
| 18.8 | 4.717 | Weak |
| 8.1 | 10.878 | Weak |
| 21.6 | 4.102 | Weak |
| 21.9 | 4.051 | Weak |
| 19.6 | 4.527 | Weak |

EXAMPLE 5

FTY720 Benzoate

Figure 3:
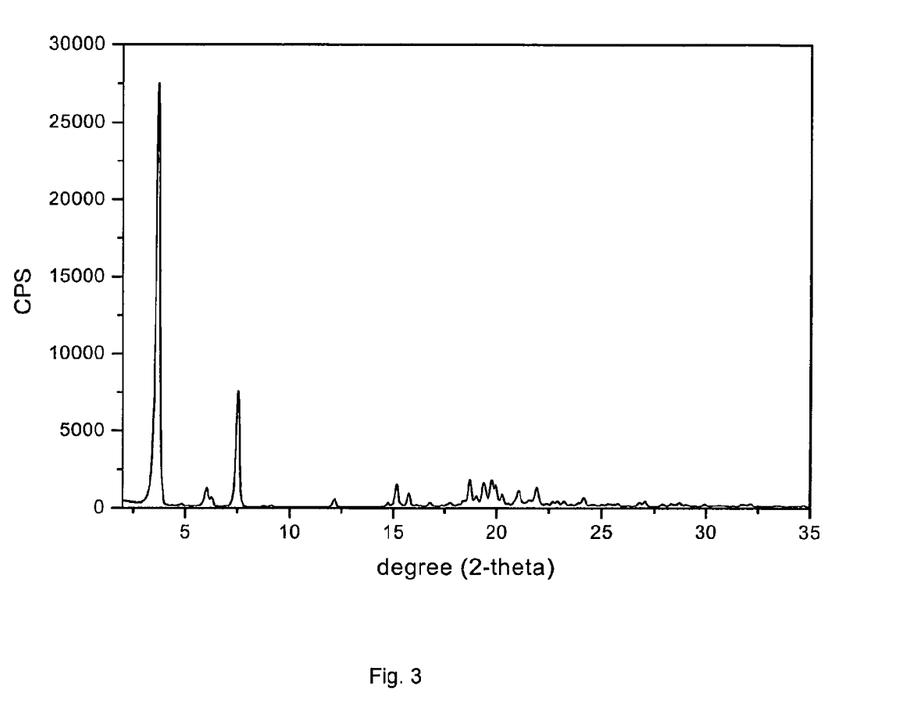

The XRPD diagram at FTY720 benzoate is shown in FIG. 3, with significant peaks given below:

| 2-theta (deg) | d-spacing (Å) | Rel. Intensity |
|---|---|---|
| 3.7 | 23.816 | Strong |
| 7.5 | 11.762 | Medium |
| 18.7 | 4.743 | Weak |
| 19.8 | 4.490 | Weak |
| 15.2 | 5.842 | Weak |
| 19.4 | 4.583 | Weak |
| 19.9 | 4.448 | Weak |
| 6.0 | 14.709 | Weak |
| 21.9 | 4.051 | Weak |

EXAMPLE 6

FTY720 Succinate (2:1)

Figure 4:
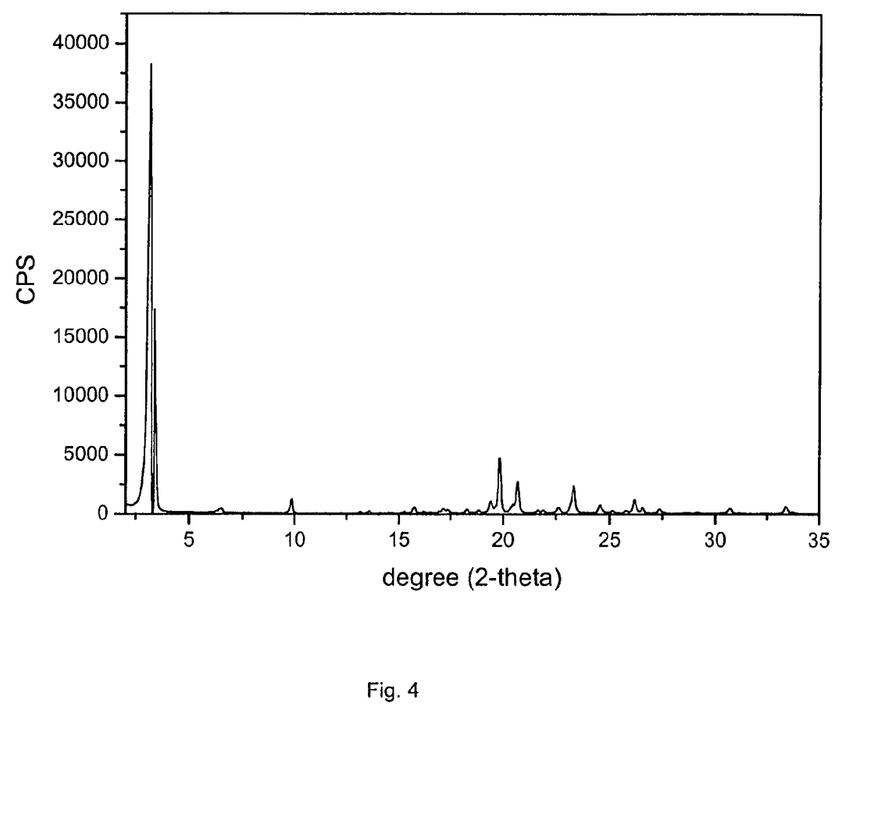

The XRPD diagram of FTY720 succinate (2:1) is given in FIG. 4, with significant peaks given below:

| 2-theta (deg) | d-spacing (Å) | Rel. Intensity |
|---|---|---|
| 3.2 | 27.952 | Strong |
| 19.8 | 4.476 | Medium |
| 20.7 | 4.294 | Weak |
| 23.3 | 3.810 | Weak |
| 26.2 | 3.403 | Weak |
| 9.8 | 8.986 | Weak |
| 19.4 | 4.571 | Weak |
| 24.5 | 3.626 | Weak |
| 33.4 | 2.681 | Weak |
| 26.6 | 3.354 | Weak |
| 22.6 | 3.929 | Weak |

EXAMPLE 7

FTY720 Malonate (2:1)

FTY720 free base (1.63 mmol) was dissolved in i-PrOH (6 ml) at 82° C. Then a solution of malonic acid (0.815 mmol) in i-PrOH (1 ml) was added at 82° C. Immediately after addition the product started to crystallize out. The suspension was cooled to room temperature. The product was collected by filtration and was washed with i-PrOH (2 ml). After drying at 50° C. the product was obtained as white crystals in 92.3% yield.

In an alternative procedure, FTY720 free base (2.27 mmol) was dissolved in ethyl acetate (16 ml) at 88 to 90° C. Then a solution of malonic acid (1.14 mmol) in ethyl acetate (3 ml) was added at 75° C., whereupon the product started to crystallize out immediately after addition. The resulting suspension was cooled to room temperature. The product was collected by filtration and was washed with ethyl acetate (2 ml). After drying at 50° C. the product (788 mg) was obtained as white crystals.

Figure 5:
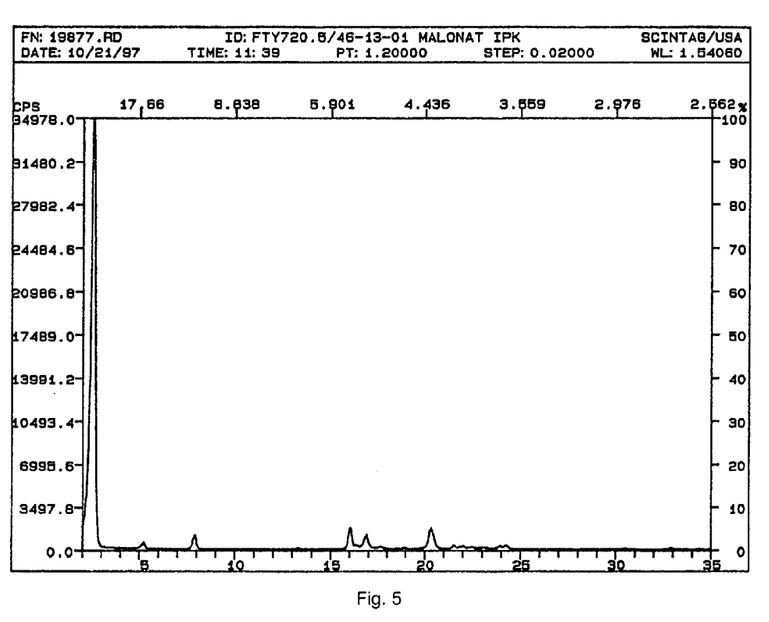

The XRPD diagram of FTY720 malonate is given in FIG. 5, with significant peaks given below:

| 2-theta (deg) | Rel. Intensity (%) |
|---|---|
| 2.5 | Strong |
| 5.2 | Weak |
| 8.0 | Weak |
| 16.2 | Weak |
| 17.0 | Weak |
| 20.4 | Weak |

EXAMPLE 8

FTY720 Acetate

FTY720 free base (1.63 mmol) was dissolved in i-PrOH (6 ml) at 82° C. Then a solution of acetic acid (1.79 eq) in i-PrOH (1 ml) was added at 82° C. The clear solution was cooled to room temperature, whereupon the product crystallized out. The resulting suspension was stirred for additional 15 minutes, the product was collected by filtration and was washed with i-PrOH (4 ml). After drying at 50° C. the crude product was obtained as white crystals in 83% yield. The product was recrystallized from a mixture of i-PrOH/acetic acid in 90.6% yield.

In an alternative procedure, FTY720 free base (2.27 mmol) was dissolved in ethyl acetate (16 ml) at 88-90° C. Then a solution of acetic acid (2.5 eq) in ethyl acetate (3 ml) was added at 75° C., whereupon the product started to crystallize out immediately after addition. The resulting suspension was cooled to room temperature. The product was collected by filtration and was washed with ethyl acetate (2 ml). After drying at 50° C. the product was obtained as white crystals in 99.4% yield.

Figure 6:
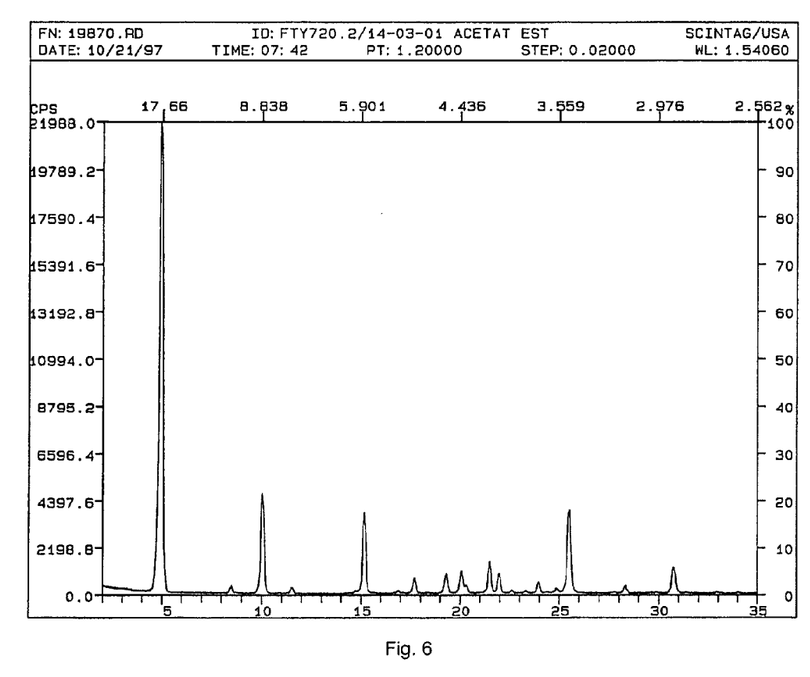

The XRPD diagram of FTY720 acetate is given in FIG. 6, with significant peaks given below:

| 2-theta (deg) | Rel. Intensity |
|---|---|
| 4.8 | Strong |
| 8.4 | Weak |
| 10.1 | Medium |
| 11.5 | Weak |
| 15.2 | Medium |
| 17.7 | Weak |
| 19.3 | Weak |
| 20.1 | Weak |
| 21.5 | Weak |
| 21.9 | Weak |
| 24.0 | Weak |
| 25.4 | Medium |
| 30.8 | weak |

EXAMPLE 9

FTY720 Propionate

FTY720 free base (1.63 mmol) was dissolved in i-PrOH (6 ml) at 82° C. Then a solution of propionic acid (1.79 eq) in i-PrOH (1 ml) was added at 82° C. The clear solution was cooled to room temperature, whereupon the product crystallized out. The resulting suspension was stirred for additional 15 minutes, the product was collected by filtration and was washed with i-PrOH (2 ml). After drying at 50° C. the crude product was obtained as white crystals in 68% yield. The product was recrystallized from a mixture of i-PrOH/propionic acid in 90.6% yield.

In an alternative procedure, FTY720 free base (2.27 mmol) was dissolved in ethyl acetate (16 ml) at 88-90° C. Then a solution of propionic acid (2.5 eq) in ethyl acetate (3 ml) was added at 70° C., whereupon the product started to crystallize out immediately after addition. The resulting suspension was cooled to room temperature. The product was collected by filtration and was washed with ethyl acetate (2 ml). After drying at 50° C. the product was obtained as white crystals in 96.9% yield.

Figure 7:
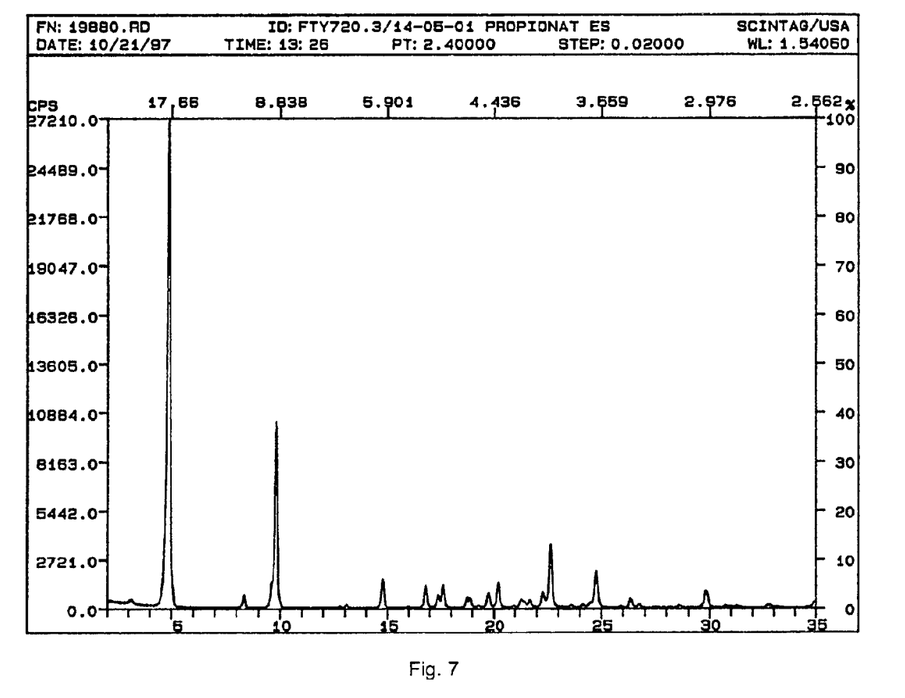

The XRPD diagram of FTY720 propionate is given in FIG. 7, with significant peaks given below:

| 2-theta (deg) | Rel. Intensity |
| --- | --- |
| 4.8 | Strong |
| 8.4 | Weak |
| 9.8 | Medium |
| 14.7 | Weak |
| 16.8 | Weak |
| 17.6 | Weak |
| 19.7 | Weak |
| 20.2 | Weak |
| 22.6 | Weak |
| 24.8 | Weak |
| 29.8 | Weak |

EXAMPLE 10

Solubility Study

The solubilities of various salts were assessed and are given in the table below (approx. values at 25° C., g/100 ml %):

| Solvent | Free Base | Hydro-chloride | Tar-trate | Lactate | Benzoate | Succinate |
| --- | --- | --- | --- | --- | --- | --- |
| 0.1N HCl | >2 | >2 | | | | >2 |
| Water | 0.018 | >10 | 0.036 | >10 | 0.036 | 0.091 |
| Ethanol | 3.88 | >7.94 | 0.07 | >7.94 | 0.97 | 0.27 |
| Isopropanol | 2.03 | 4.51 | 0.09 | 2.75 | 0.35 | 0.23 |
| Acetone | 0.52 | 0.08 | 0.06 | 1.3 | 0.36 | 0.09 |
| Octanol | 1-2 | 1-2 | | | | <0.1 |
| Ethylacetate | 0.45 | 0.03 | 0.05 | 0.31 | 0.08 | 0.07 |
| pH 6.88 phosphate buffer | <0.001 | <0.001 | | | | <0.001 |

The invention claimed is:

1. A tartrate salt of 2-amino-2-(2-(4-octylpheny)ethyl)propane-1,3-diol (FTY720), wherein the salt is in crystalline form characterized by an X-ray powder diffraction pattern with peaks at about 3.1, 19.3, 21.7, 9.6, 17.2, 6.4, 22.6 and 20.8 degrees 2-theta.

2. A lactate salt of 2-amino-2-(2-(4-octylphenyl)ethyl)propane-1,3-diol (FTY720), wherein the salt is in crystalline form characterized by an X-ray powder diffraction pattern with peaks at about 4.3, 8.7, 20.8, 13.1, 10.3, 18.8, 8.1, 21.6, 21.9 and 19.6 degrees 2-theta.

3. A benzoate salt of 2-amino-2-(2-(4-octylphenyl)ethyl)propane-1,3-diol (FTY720), wherein the salt is in crystalline form characterized by an X-ray powder diffraction pattern with peaks at about 3.7, 7.5, 18.7, 19.8, 15.2, 19.4, 19.9, 6.0 and 21.9 degrees 2-theta.

4. A sucinate salt of 2-amino-2-(2-(4-octylphenyl)ethyl)propane-1,3-diol (FTY720), wherein the salt is in crystalline form characterized by an X-ray powder diffraction pattern with peaks at about 3.2, 19.8, 20.7, 23.3, 26.2, 9.8, 19.4, 24.5, 33.4, 26.6 and 22.6 degrees 2-theta.

5. A malonate salt of 2-amino-2-(2-(4-octylphenyl)ethyl)propane-1,3-diol (FTY720), wherein the salt is in crystalline form characterized by an X-ray powder diffraction pattern with peaks at about 2.5, 52, 8.0, 16.2, 17.0, 20.4 degrees 2-theta.

6. A acetate salt of 2-amino-2-(2-(4-octylphenyl)ethyl)propane-1,3-diol (FTY720), wherein the salt is in crystalline form characterized by an X-ray powder diffraction pattern with peaks at about 4.8, 8.4, 10.1, 11.5, 15.2, 17.7, 19.3, 20.1, 21.5, 21.9, 24.0, 25.4, 30.8 degrees 2-theta.

7. A propionate salt of 2-amino-2-(2-(4-octylphenyl)ethyl)propane-1,3-diol (FTY720), wherein the salt is in crystalline form characterized by an X-ray powder diffraction pattern with peaks at about 4.8, 8.4, 9.8, 14.7, 16.8, 17.6, 19.7, 20.2, 22.6, 24.8, 29.8 degrees 2-theta.

* * * * *